(12) United States Patent
Okubo

(10) Patent No.: US 8,501,234 B2
(45) Date of Patent: Aug. 6, 2013

(54) REVERSE VESICLE

(75) Inventor: Koji Okubo, Tokyo (JP)

(73) Assignee: Kao Corporation, Tokyo (JP)

( * ) Notice: Subject to any disclaimer, the term of this patent is extended or adjusted under 35 U.S.C. 154(b) by 207 days.

(21) Appl. No.: 12/672,124

(22) PCT Filed: Aug. 8, 2008

(86) PCT No.: PCT/JP2008/002176
§ 371 (c)(1),
(2), (4) Date: Feb. 4, 2010

(87) PCT Pub. No.: WO2009/019891
PCT Pub. Date: Feb. 12, 2009

(65) Prior Publication Data
US 2011/0263714 A1 Oct. 27, 2011

(30) Foreign Application Priority Data

Aug. 9, 2007 (JP) ................. 2007-207539

(51) Int. Cl.
*A61K 9/14* (2006.01)
*A61K 9/16* (2006.01)
*A61K 8/68* (2006.01)
*A61K 31/133* (2006.01)
*A61K 8/06* (2006.01)

(52) U.S. Cl.
CPC ............. *A61K 8/68* (2013.01); *A61K 31/133* (2013.01); *A61K 9/14* (2013.01); *A61K 9/16* (2013.01); *A61K 8/064* (2013.01)
USPC ........................ 424/489; 424/450; 424/455

(58) Field of Classification Search
None
See application file for complete search history.

(56) References Cited

U.S. PATENT DOCUMENTS

| 5,716,639 A | 2/1998 | Carlsson et al. | |
|---|---|---|---|
| 2005/0112082 A1* | 5/2005 | Hoshino et al. | 424/70.31 |
| 2005/0163742 A1* | 7/2005 | Okubo et al. | 424/70.27 |

FOREIGN PATENT DOCUMENTS

JP   9-508415 A   8/1997

OTHER PUBLICATIONS

MF Kemmere, J Leuldijk, AAH Drinkenburg, AL German. "Emulsification in Batch-Emulsion Polymerization of Styrene and Vinyl Acetate: A Reaction Calorimetric Study." Journal of Applied Polymer Science, vol. 79, 2001, pp. 944-957.*

Office actions, replies and certain other documents from the file history of U.S. Appl. No. 10/863,491.
International Search Report for PCT/JP2008/002176, English language translation with Japanese language version attached, mailed Nov. 18, 2008, Japanese Patent Office, Tokyo, Japan.
Written Opinion of the International Searching Authority for PCT/JP2008/002176, mailed Nov. 18, 2008, The International Bureau of WIPO, Geneva, Switzerland.
International Preliminary Report on Patentability for PCT/JP2008/002176, mailed Feb. 24, 2010, The International Bureau of WIPO, Geneva, Switzerland.
Kunieda, H. et al., "Formation of Vesicles and Microemulsions in a Water/Tetraethylene Glycol Dodecyl Ether/Dodecane System," *Langmuir* 7: 1915-1919 (1991), American Chemical Society, Washington, DC.
Nakamura, K. et al., "Normal and reverse Vesicles with Nonionic Surfactant: Solvent Diffusion and Permeability," *Langmuir 12*: 3045-3054 (1996), American Chemical Society, Washington, DC.
Kunieda, H. et al., "Formation of Reversed Vesicles," *J. Am Chem. Soc.113*:1051-1052 (1991), American Chemical Society, Washington, DC.
Kunieda, H. et al., "Spontaneous Formation of Reverse Vesicles," *J. Phys. Chem.* 97:9525-9531 (1993), American Chemical Society, Washington, DC.
Prosecution documents from the file history of U.S. Appl. No. 10/863,491.
"Notice of Reasons for Rejection," for JP Patent Application No. 2008-205429, mailed Dec. 4, 2012, Japanese Patent Office, Tokyo, Japan.

* cited by examiner

*Primary Examiner* — Frederick Krass
*Assistant Examiner* — Isaac Shomer
(74) *Attorney, Agent, or Firm* — Sterne, Kessler, Goldstein & Fox P.L.L.C.

(57) ABSTRACT

The reverse vesicle composition of the present invention includes (A) a sphingosine represented by formula (I),
(B) a C16 to C30 fatty acid,
(C) a hydrocarbon oil,
(D) an ester oil which is in liquid form at 25° C., and
(F) water,
wherein the ratio by mass of ingredient (C) to ingredient (D) satisfies the following relationship: $1 \leq (C)/(D) < 1000$, and the composition contains a surfactant having a molecular weight of 1,000 or less in an amount of 1 mass % or less.

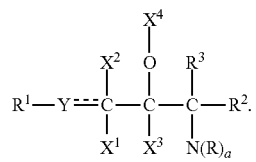

(1)

15 Claims, No Drawings

REVERSE VESICLE

FIELD OF THE INVENTION

The present invention relates to a reverse vesicle composition.

BACKGROUND OF THE INVENTION

The human stratum corneum, in which intercellular lipid forms a lamellar structure, is known to play an important role in barrier and moisturizing functions. Thus, in the production of skin agents for external application such as creams and emulsions, there is demand for a pharmaceutical product which enhances such functions and improves skin conditions.

From the viewpoint of enhancing barrier and moisturizing functions, a pharmaceutical product having the same lamellar structure as that of the skin is desired for the enhancement of skin permeability and moisturizing effect. Since the structure of a pharmaceutical product having a vesicle structure is similar to the structure of intercellular lipids in stratum corneum, such a pharmaceutical product is thought to have higher functions in terms of skin permeability, moisturizing effect, etc.

Hitherto, it has been known that vesicle compositions in which a continuous phase is an oily phase have been rarely employed. The only examples are a reverse vesicle formed of a nonionic surfactant, oil, and water (Non-Patent Document 1), and a water-free reverse vesicle containing sucrose monoalkanoate, hexaethylene glycerol hexadecyl ether, and heptane (Non-Patent Document 2).

However, reverse vesicle compositions having a lamellar structure have considerably poor stability, since the electrostatic repulsion force cannot be attained due to an oily continuous phase, which is problematic.

[Non-Patent Document 1]
Hironobu Kunieda et al., Langmuir, 1991, 7, 1915-1919

[Non-Patent Document 2]
Hironobu Kunieda et al., J. Phys. Chem., 1993, 97, 9525-9531

SUMMARY OF THE INVENTION

The present invention provides a reverse vesicle composition which has excellent stability and provides good sensation in use.

The present inventor has found that, through use of the combination of a sphingosine, which is originally present in the skin, a salt derived from a specific fatty acid serving as an emulsifying agent, a hydrocarbon oil, and an ester oil, in specific compositional proportions, there can be produced a reverse vesicle composition which is stable for a long period, provides good sensation in use thereof, and exhibits an excellent moisturizing effect.

The present invention provides a reverse vesicle composition having the following ingredients (A), (B), (C), (D), and (F):

(A) a sphingosine represented by formula (1):

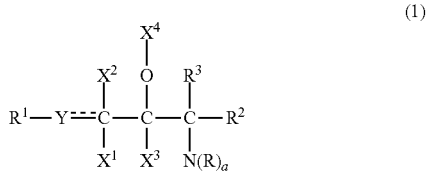

(wherein $R^1$ represents a C4 to C30 linear alkyl group which may be substituted by a hydroxyl group, a carbonyl group, or an amino group; Y represents a methylene group, a methine group, or an oxygen atom; each of $X^1$, $X^2$, and $X^3$ represents a hydrogen atom, a hydroxyl group, or an acetoxy group; $X^4$ represents a hydrogen atom, an acetyl group, or a glyceryl group, or forms an oxo group together with the adjacent oxygen atom (wherein when Y is a methine group, one of X' and $X^2$ is a hydrogen atom, and the other is absent, and when $X^4$ forms an oxo group, $X^3$ is absent); each of $R^2$ and $R^3$ represents a hydrogen atom, a hydroxyl group, a hydroxymethyl group, or an acetoxymethyl group; a is a number of 2 or 3; each of $(R)_a$ represents a hydrogen atom, an amidino group, or a linear alkyl group optionally having a substituent selected from among a hydroxyl group, a hydroxyalkoxy group, an alkoxy group, and an acetoxy group and containing 1 to 8 carbon atoms in total; and the broken line represents an optional unsaturated bond), (B) a C16 to C30 fatty acid,
(C) a hydrocarbon oil,
(D) an ester oil which is in liquid form at 25° C., and
(F) water, wherein the ratio by mass of ingredient (C) to ingredient (D) satisfies the following relationship: $1 \leq (C)/(D) < 1000$, and the composition contains a surfactant having a molecular weight of 1,000 or less in an amount of 1 mass % or less.

The present invention also provides a method for producing the reverse vesicle composition.

As used herein, the term "reverse vesicle" refers to a microstructure containing an oil phase surrounded by a bilayer membrane formed of a lipid or an amphipathic compound having a hydrophilic moiety and a lipophilic moiety. The term "reverse vesicle structure" refers to a structure in which the hydrophobic moiety of the amphipathic compound having a hydrophilic moiety and a lipophilic moiety is aligned so as to face the oil phase, and the hydrophilic moiety forms the inner structure of the bilayer membrane.

The reverse vesicle composition of the present invention is stable in a wide temperature range (from low to high), provides good sensation in use thereof, easily permeates the skin, and exhibits an excellent moisturizing effect.

DETAILED DESCRIPTION OF THE INVENTION

The sphingosine serving as the ingredient (A) employed in the present invention is represented by the aforementioned formula (1).

In formula (1), $R^1$ is a C4 to C30 linear alkyl group which may be substituted by a hydroxyl group, a carbonyl group, or an amino group, preferably a C7 to C24 linear alkyl group which may be substituted by a hydroxyl group. More preferred are a C10 to C24 linear alkyl group and a C10 to C24 linear alkyl group having a hydroxyl group on the carbon atom bonding to Y in formula (1). Specific examples of preferred alkyl groups include tridecyl, tetradecyl, pentadecyl, hexadecyl, 1-hydroxytridecyl, and 1-hydroxypentadecyl.

Y represents a methylene group ($CH_2$), a methine group (CH), or an oxygen atom.

Each of $X^1$, $X^2$, and $X^3$ is a hydrogen atom, a hydroxyl group, or an acetoxy group. $X^4$ is a hydrogen atom, an acetyl group, or a glyceryl group, or a substituent which forms an oxo group together with the adjacent oxygen atom. In a preferred embodiment, 0 to 1 of $X^1$, $X^2$, and $X^3$ is a hydroxyl group, and the remaining groups are a hydrogen atom, and $X^4$ is a hydrogen atom. When Y is a methine group, one of $X^1$ and $X^2$ is a hydrogen atom, and the other is absent. When $X^4$ forms an oxo group, $X^3$ is absent.

Each of $R^2$ and $R^3$ is a hydrogen atom, a hydroxyl group, a hydroxymethyl group, or an acetoxymethyl group. $R^3$ is preferably a hydrogen atom.

The number of "a" is 2 or 3. When a is 2, $R^5$ correspond to $R^4$ and $R^5$, and when a is 3, $R^5$ correspond to $R^4$, $R^5$, and $R^6$.

Each of $R^4$, $R^5$, and $R^6$ represents a hydrogen atom, an amidino group, or a linear-chain alkyl group optionally having a substituent selected from among a hydroxyl group, a hydroxyalkoxy group, an alkoxy group, and an acetoxy group and containing 1 to 8 carbon atoms in total. The hydroxyalkoxy group which may be substituted by an alkyl group is preferably a C1 to C7 linear or branched hydroxyalkoxy group. The alkoxy is preferably a C1 to C7 linear or branched alkoxy group. Examples of $R^4$, $R^5$, and $R^6$ include hydrocarbon groups each having 1 to 8 carbon atoms in total and being substituted by 1 to 6 substituents. Examples of the substituents include a hydrogen atom; linear- or branched-alkyl groups such as methyl, ethyl, propyl, 2-ethylhexyl, and iso-propyl; alkenyl groups such as vinyl and allyl; an amidino group; hydroxyl groups such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl; hydroxyalkoxy groups, and alkoxy groups.

Among them, more preferred are a hydrogen atom and alkyl groups each being substituted by 1 to 3 groups selected from among methyl, hydroxyl groups such as 2-hydroxyethyl, 1,1-dimethyl-2-hydroxyethyl, 1,1-bis(hydroxymethyl)ethyl, and 2-(2-hydroxyethoxy)ethyl, and hydroxyalkoxy groups.

The sphingosine represented by formula (1) is preferably a natural or natural-type sphingosine represented by formula (3):

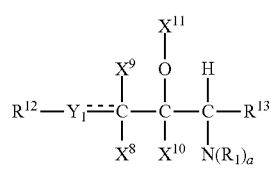

(3)

(wherein $R^{12}$ represents a C7 to C24 linear alkyl group which may be substituted by a hydroxyl group; $Y_1$ represents a methylene group or a methine group; each of $X^8$, $X^9$, and $X^{10}$ represents a hydrogen atom, a hydroxyl group, or an acetoxy group; $X^{11}$ represents a hydrogen atom or forms an oxo group together with the adjacent oxygen atom (wherein when $Y_1$ is a methine group, one of $X^8$ and $X^9$ is a hydrogen atom, and the other is absent, and when $X^{11}$ forms an oxo group, $X^{10}$ is absent); $R^{13}$ represents a hydroxymethyl group or an acetoxymethyl group; a is a number of 2 or 3; each of $(R_1)_a$ represents a hydrogen atom, an amidino group, or a linear alkyl group optionally having a substituent selected from among a hydroxyl group, a hydroxyalkoxy group, an alkoxy group, and an acetoxy group and containing 1 to 4 carbon atoms in total; and the broken line represents an optional unsaturated bond) or a derivative thereof (hereinafter, these compounds are collectively referred to as "natural sphingosine").

The group $R^{12}$ is preferably a C7 to C24 linear alkyl group, more preferably a C13 to C24 linear alkyl group. The number of "a" is preferably 2, and each of $(R_1)_a$ is preferably a hydrogen atom or a C1 to C4 linear alkyl group.

Specific examples of the natural sphingosine represented by formula (3) include sphingosine, dihydrosphingosine, phytosphingosine, sphingadienine, dehydrosphingosine, and dehydrophytosphingosine, which are all naturally occurring compounds, and N-alkyl derivatives thereof (e.g., N-methyl derivatives).

Regarding these sphingosines, either a natural type optically active form (D(+) form) or a non-natural type optically active form (L(−) form) may be used. Furthermore, a mixture of a natural type form and a non-natural type form may also be used. The relative configuration of the aforementioned compound may be of natural type, of non-natural type, or of mixed type.

Examples of preferred sphingosines further include phytosphingosine (INCI nomenclature; 8th Edition) and the compounds represented by the following formulas.

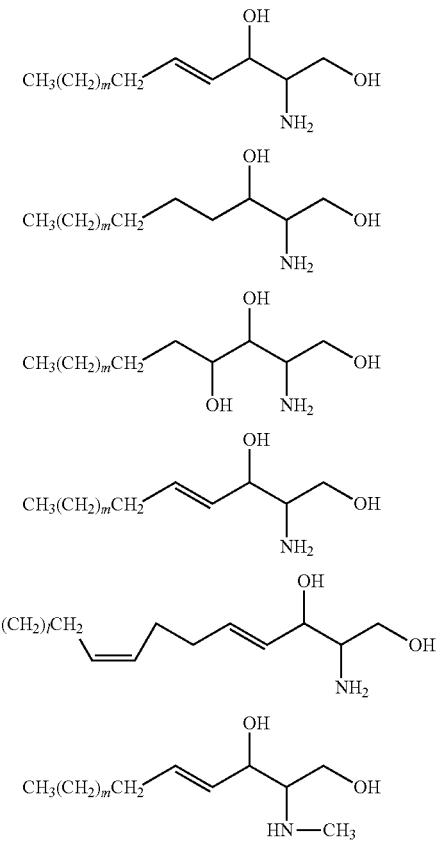

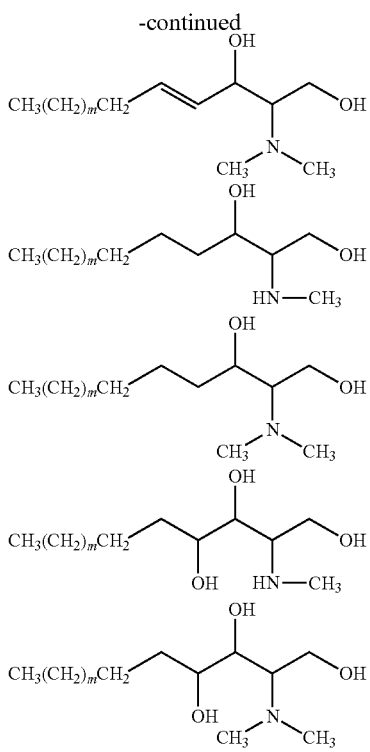

m = 15 to 17, l = 1 to 13

These compounds may be a natural extract or a synthetic compound, and a commercial product thereof may be used.

Examples of the commercial product of natural sphingosine include D-sphingosine (4-sphingenine) (product of SIGMA-ALDRICH), DS-phytosphingosine (product of DOOSAN), and phytosphingosine (product of COSMOFERM).

The sphingosine of ingredient (A) forms with the below-described ingredient (B) an amphipathic salt having a hydrophilic moiety and a lipophilic moiety. The salt serves an ingredient forming a bilayer membrane in the below-described ingredients (C) and (D).

One or more species of ingredient (A) may be used. The total ingredient (A) content of the composition is preferably 0.001 to 10 mass %, more preferably 0.005 to 3 mass %, even more preferably 0.01 to 3 mass %, from the viewpoints of formation of the reverse vesicle and the stability of the formed reverse vesicle.

The fatty acid of ingredient (B) employed in the present invention forms a salt through acid-base neutralization with an amine group(s) of the sphingosine, to thereby cationize the sphingosine, forming a hydrophilic moiety. The thus-formed salt is thought to serve as an agent like a surfactant. The thus-formed sphingosine salt may be identified through a conventional method for determining the structure of a compound; such as infrared absorption spectrometry or proton nuclear magnetic resonance spectrometry.

The fatty acid serving as ingredient (B) is required to have 16 to 30 carbon atoms. From the viewpoints of easy formation of a bilayer membrane of the vesicle composition, a C16 to C22 saturated or unsaturated fatty acid is preferred. When a C16 to C30 fatty acid is employed, a reverse vesicle composition which is stable in a mixed-type oil medium can be produced. Specific examples of the fatty acid include saturated fatty acids such as palmitic acid, stearic acid, eicosanoic acid, and behenic acid; and unsaturated fatty acids such as oleic acid, linoleic acid, linolenic acid, recinoleic acid, eicosapentaenoic acid, and docosahexaenoic acid.

Of these, C16 to C22 linear-chain saturated fatty acids are preferred, with palmitic acid, stearic acid, and behenic acid being more preferred, from the viewpoints of good sensation of use of the composition and stability of the composition.

One or more species of the fatty acids of ingredient (B) may be used. The total ingredient (B) content of the composition is preferably 0.001 to 10 mass %, more preferably 0.005 to 6 mass %, even more preferably 0.01 to 3 mass %, from the viewpoints of formation of bilayer membrane and the stability of the formed reverse vesicle.

In order to cationize the amine group(s) of the sphingosine serving as ingredient (A), the composition of the present invention preferably contain ingredient (B) in an amount of 0.3 mol or more with respect to 1 mole of ingredient (A), more preferably 0.3 to 5 mol, even more preferably 0.5 to 3 mol, from the viewpoints of formation of reverse vesicle and the stability of the formed reverse vesicle.

The hydrocarbon oil serving as ingredient (C) employed in the present invention includes those which are in the liquid, semi-solid, or solid form at 25° C. and are synthetic or natural products. Examples of the liquid hydrocarbon oil include liquid lanolin, liquid paraffin, liquid isoparaffin, α-olefin oligomer, polybutene, hydrogenated polyolefin, and squalane, and examples of the semi-solid or solid hydrocarbon oil include waxes such as vaseline, lanolin, ceresine, and microcrystalline wax.

Among them, liquid hydrocarbon oils are preferred, with liquid isoparaffin, α-olefin oligomer, polybutene, squalane, etc. being more preferred, from the viewpoint of the stability of reverse vesicle.

One or more species of the hydrocarbon oil of ingredient (C) may be used. The total ingredient (C) content of the composition is preferably 0.1 to 50 mass %, more preferably 0.1 to 30 mass %, even more preferably 1 to 15 mass %, from the viewpoint of the stability of the formed reverse vesicle.

The ester oil which is in liquid form at 25° C. serving as ingredient (D) employed in the present invention is preferably an ester of a fatty acid with cholesterol, a C12 to C22 higher alcohol, an alcohol having carbon atoms of 4 or less, or a polyhydric alcohol. Examples of such an ester include diisostearyl malate, octyldodecyl lactate, isopropyl palmitate, diisopropyl adipate, propylene glycol dicaprate, octyl isononanoate, phytosteryl isostearate, glyceryl triundecylate, glyceryl triisopalmitate, isotridecyl isononanoate, isopropyl isostearate, octyldodecyl myristate, and cholesterol isostearate. However, the ester (D) does not include esters formed from a sugar and a fatty acid.

Among them, isopropyl palmitate, diisopropyl adipate, propylene glycol dicaprate, octyl isononanoate, phytosteryl isostearate, glyceryl triundecylate, glyceryl triisopalmitate, and cholesterol isostearate are preferred.

One or more species of the ester oil of ingredient (D) may be used. The total ingredient (D) content of the composition is preferably 0.01 to 50 mass %, more preferably 0.01 to 30 mass %, even more preferably 0.1 to 15 mass %, from the viewpoint of the stability of the formed reverse vesicle.

In the present invention, the ratio by mass of ingredient (C) to ingredient (D) satisfies the following relationship: $1 \leq (C)/(D) < 1000$, preferably $9 \leq (C)/(D) \leq 70$, more preferably $9 \leq (C)/(D) \leq 10$.

Through controlling the ratio by mass (C)/(D) to fall within the aforementioned ranges, the amphipathic compound formed from ingredients (A) and (B) yields a robust bilayer membrane, and a reverse vesicle composition having high stability can be produced.

The composition of the present invention may further contain (E) a ceramide. The ceramide is preferably employed, since it aligns at the interface in the bilayer membrane formed of an amphipathic compound produced from ingredients (A) and (B), to thereby further enhance the stability of the formed reverse vesicle.

The ceramide is preferably a compound represented by formula (2):

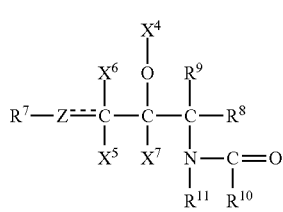

(2)

(wherein $R^7$ represents a hydrogen atom or a C4 to C30 linear, branched or cyclic, saturated or unsaturated hydrocarbon group which may be substituted by a hydroxyl group, a carbonyl group, or an amino group; Z represents a methylene group, a methine group, or an oxygen atom; each of $X^5$, $X^6$, and $X^7$ represents a hydrogen atom, a hydroxyl group, or an acetoxy group; $X^4$ represents a hydrogen atom, an acetyl group, or a glyceryl group, or forms an oxo group together with the adjacent oxygen atom (wherein when Z is a methine group, one of $X^5$ and $X^6$ is a hydrogen atom, and the other is absent, and when $X^4$ forms an oxo group, $X^7$ is absent); each of $R^8$ and $R^9$ represents a hydrogen atom, a hydroxyl group, a hydroxymethyl group, or an acetoxymethyl group; $R^{10}$ represents a C5 to C60 linear-chain, branched-chain or cyclic, saturated or unsaturated hydrocarbon group which may be substituted by a hydroxyl group, a carbonyl group, or an amino group, and which may have an ether bond, an ester bond, or an amido bond in a main chain thereof; $R^{11}$ represents a hydrogen atom or a linear-chain or branched-chain, saturated or unsaturated hydrocarbon group optionally having a substituent selected from among a hydroxyl group, a hydroxyalkoxy group, an alkoxy group, and an acetoxy group and containing 1 to 30 carbon atoms in total (wherein, when $R^7$ is a hydrogen atom and Z is an oxygen atom, $R^{11}$ is a hydrocarbon group having 10 to 30 carbon atoms in total, and when $R^7$ is a hydrocarbon group, $R^{11}$ is a hydrocarbon group having 1 to 8 carbon atoms in total); and the broken line represents an optional unsaturated bond).

In formula (2), $R^7$ is a hydrogen atom or a linear, branched or cyclic, saturated or unsaturated hydrocarbon group optionally having a substituent selected from among a hydroxyl group, a carbonyl group, or an amino group (preferably a hydroxyl group) and containing 4 to 30 (preferably 7 to 22) carbon atoms in total.

Z represents a methylene group, methine group, or an oxygen atom.

Each of $X^5$, $X^6$, and $X^7$ represents a hydrogen atom, a hydroxyl group, or an acetoxy group. Preferably, 0 to 1 of $X^5$, $X^6$, and $X^7$ is a hydroxyl group, and each remaining group is a hydrogen atom. When Z is a methine group, only one of $X^5$ and $X^6$ is a hydrogen atom, and the other is absent. $X^4$ is preferably a hydrogen atom or a glyceryl group.

Each of $R^8$ and $R^9$ is a hydrogen atom, a hydroxyl group, a hydroxymethyl group, or an acetoxymethyl group. Preferably, $R^8$ is a hydrogen atom or a hydroxymethyl group, and $R^9$ is a hydrogen atom.

$R^{10}$ represents a C5 to C60 linear, branched, or cyclic, saturated or unsaturated hydrocarbon group which may be substituted by a hydroxyl group, a carboxyl group, or an amino group, and which may have an ether bond, an ester bond, or an amido bond in a main chain thereof. $R^{10}$ is preferably a C5 to C35 linear-chain, branched-chain, or cyclic, saturated or unsaturated hydrocarbon group which may be substituted by a hydroxyl group or an amino group, or such a hydrocarbon group to which a C8 to C22 linear, branched, or cyclic, saturated or unsaturated fatty acid which may be substituted by a hydroxyl group is bonded at the ω-position via ester bonding or amido bonding. The fatty acid bonding to $R^{10}$ is preferably isostearic acid, 12-hydroxystearic acid, or linoleic acid.

$R^{11}$ represents a hydrogen atom or a linear or branched, saturated or unsaturated hydrocarbon group optionally having a substituent selected from among a hydroxyl group, a hydroxyalkoxy group, an alkoxy group, and an acetoxy group and containing 1 to 30 carbon atoms in total. When $R^7$ is a hydrogen atom and Z is an oxygen atom, $R^{11}$ is a hydrocarbon group having 10 to 30 carbon atoms in total. When $R^7$ is a hydrocarbon group, $R^{11}$ is a hydrocarbon group having 1 to 8 carbon atoms in total. $R^{11}$ is preferably a hydrogen atom, or a hydrocarbon group having 1 to 8 carbon atoms in total which group may be substituted by 1 to 3 substituents selected from among a hydroxyl group, a hydroxyalkoxy group, and an alkoxy group. Preferably, the hydroxyalkoxy group and the alkoxy group each have 1 to 7 carbon atoms.

The ceramide represented by formula (2) is preferably a ceramide represented by the following formula (4) or (5).

(I): Natural or natural-type ceramide and derivatives thereof (hereinafter referred to as "natural ceramide") represented by formula (4):

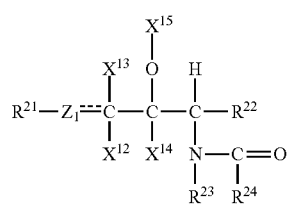

(4)

(wherein $R^{21}$ represents a C7 to C19 linear, branched or cyclic, saturated or unsaturated hydrocarbon group which may be substituted by a hydroxyl group; $Z_1$ represents a methylene group or a methine group; each of $X^{12}$, $X^{13}$, and $X^{14}$ represents a hydrogen atom, a hydroxyl group, or an acetoxy group; $X^{15}$ represents a hydrogen atom, or forms an oxo group together with the adjacent oxygen atom (wherein when $Z_1$ is a methine group, one of $X^{12}$ and $X^{13}$ is a hydrogen atom, and the other is absent, and when $X^{15}$ forms an oxo group, $X^{14}$ is absent); $R^{22}$ represents a hydroxymethyl group or an acetoxymethyl group; $R^{23}$ represents a hydrogen atom or a C1 to C4 alkyl group; $R^{24}$ represents a C5 to C30 linear, branched or cyclic, saturated or unsaturated hydrocarbon group which may be substituted by a hydroxyl group, or such an alkyl group to which a C8 to C22 linear or branched, saturated or unsaturated fatty acid which may be substituted by a hydroxyl group is bonded at the co-end via ester bonding; and the broken line represents an optional unsaturated bond).

In a preferred compound, $R^{21}$ is a C7 to C19 (more preferably C13 to C15) linear alkyl group; $R^{24}$ is a C9 to C27 linear alkyl group which may be substituted by a hydroxyl group, or a C9 to C27 linear alkyl group to which linoleic acid is bonded via ester bonding. Preferably, $X^{15}$ is a hydrogen atom or forms an oxo group together with an oxygen atom. $R^{24}$ is preferably tricosyl, 1-hydroxypentadecyl, 1-hydroxytricosyl, heptadecyl, 1-hydroxyundecyl, or nonacosyl to which linoleic acid is bonded at the co-position via ester bonding.

Specific examples of the natural ceramide include sphingosine, dihydrosphingosine, phytosphingosine, and amidated sphingadienines (ceramides of Types 1 to 7) (see, for example, pig-origin and human-origin ceramides shown in FIG. 2 in J. Lipid Res., 24: 759 (1983) and FIG. 4 in J. Lipid. Res., 35: 2069 (1994)).

The ceramides also encompass N-alkyl forms (e.g., N-methyl form) thereof.

Regarding these ceramides, either a natural type optically active form (D(−) form) or a non-natural type optically active form (L(+) form) may be used. Furthermore, a mixture of a natural type form and a non-natural type form may also be used. The relative configuration of the aforementioned compound may be of natural type, of non-natural type, or of mixed type. Further, preferred are compounds: CERAMIDE 1, CERAMIDE 2, CERAMIDE 3, CERAMIDE 5, CERAMIDE 611, (INCI, 8th Edition), and those represented by the following formulas.

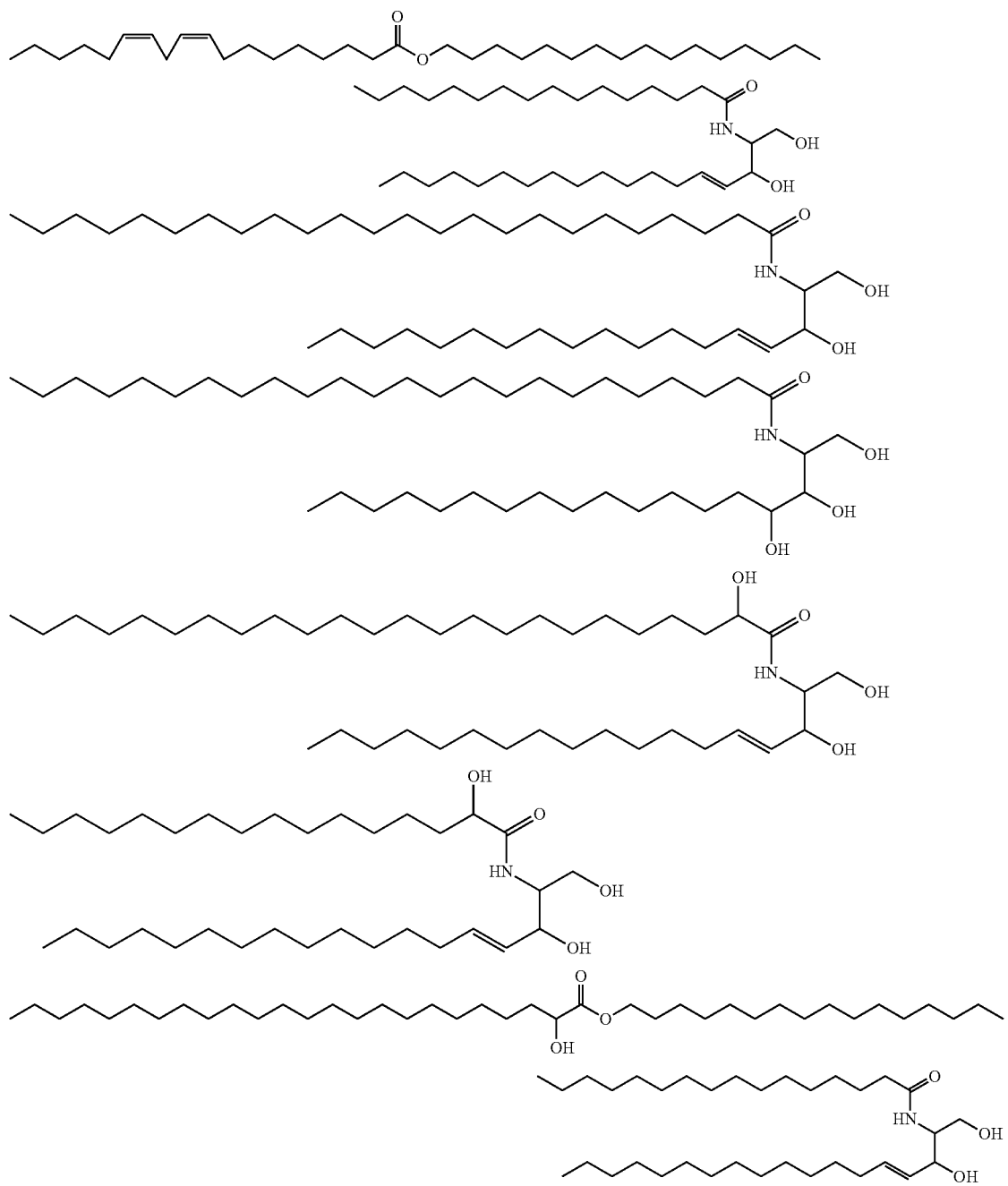

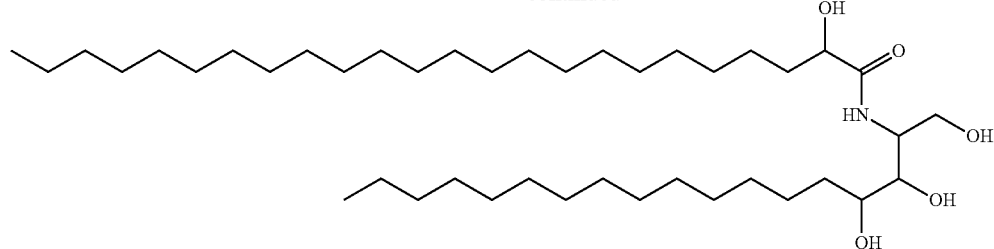

These ceramides may be natural extracts or synthetic products. Commercial products thereof may also be employed in the invention.

Examples of such natural ceramide commercial products include Ceramide I, Ceramide III, Ceramide IIIA, Ceramide IIIB, Ceramide IIIC, and Ceramide VI (COSMOFERM); Ceramide TIC-001 (Takasago International Corporation); CERAMIDE II (Quest International); DS-Ceramide VI, DS-CLA-Phytoceramide, C6-Phytoceramide, and DS-ceramide Y3S (DOOSAN); and CERAMIDE2 (Sederma).

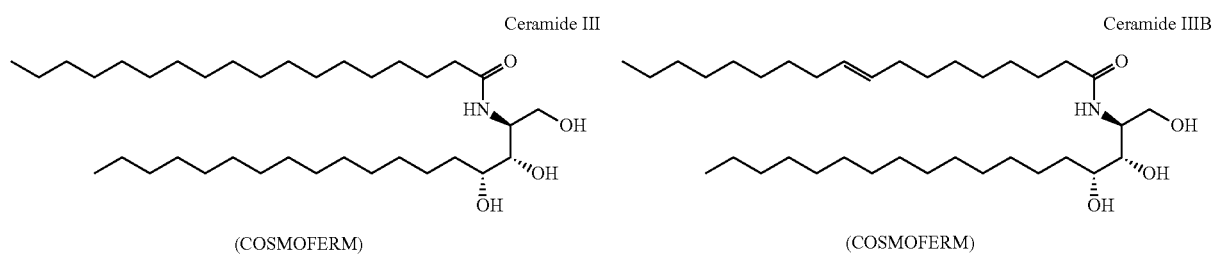

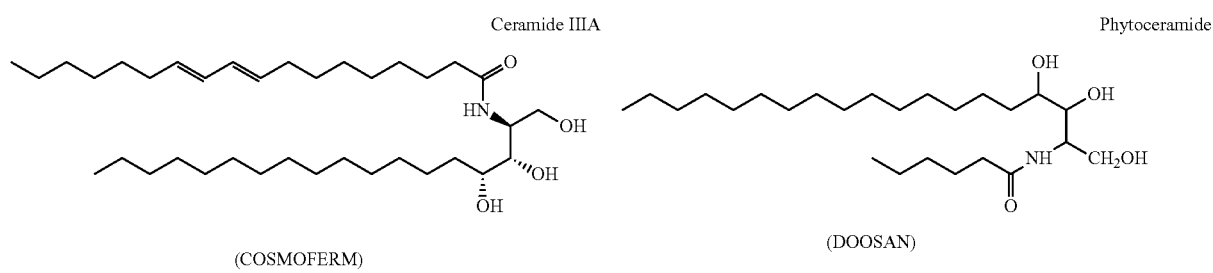

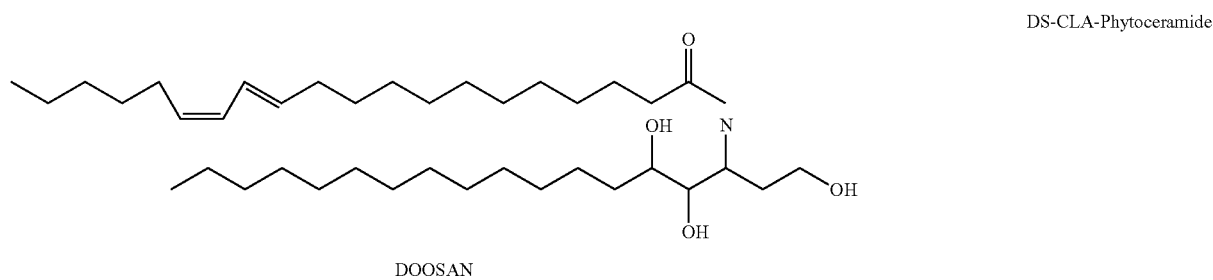

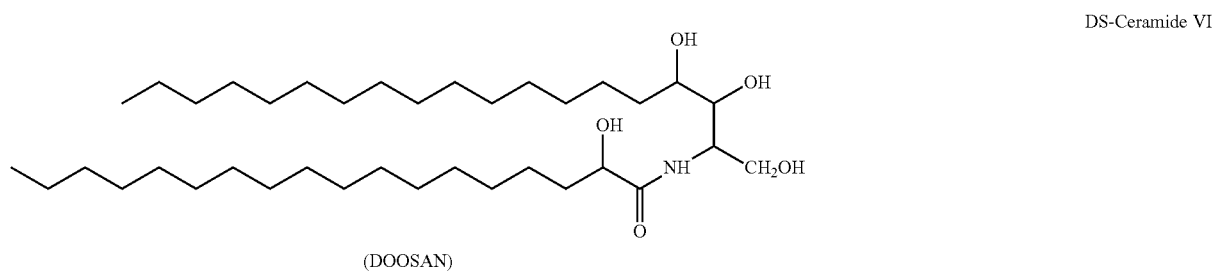

-continued

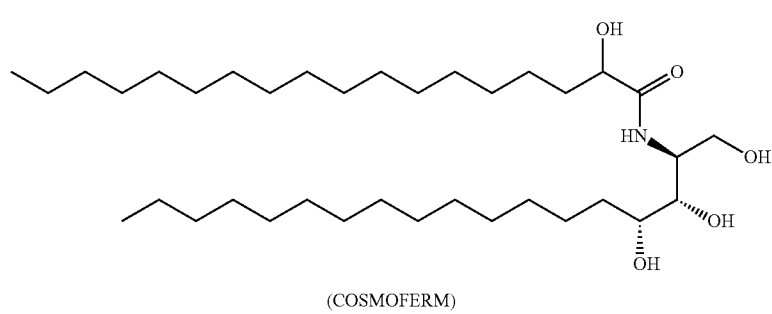
(COSMOFERM) Ceramide IV

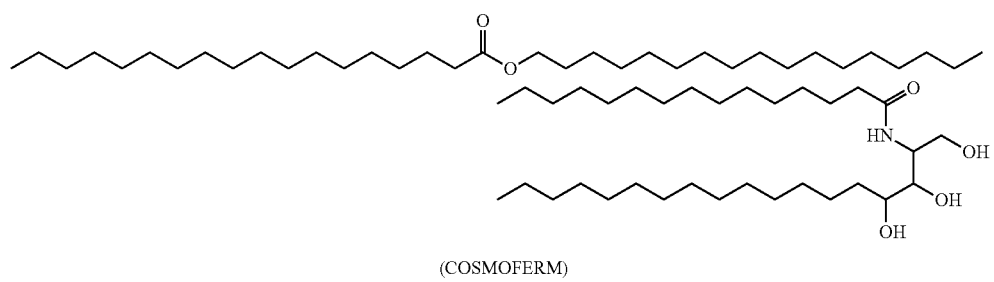
(COSMOFERM) Ceramide I (II): Pseudo-ceramides represented by formula (5):

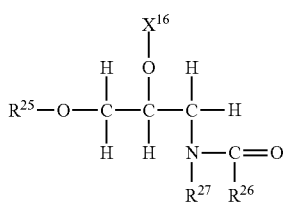

(5)

(wherein $R^{25}$ represents a hydrogen atom or a C10 to C22 linear, branched, or cyclic, saturated or unsaturated hydrocarbon group which may be substituted by a hydroxyl group; $X^{16}$ represents a hydrogen atom, an acetyl group, or a glyceryl group; $R^{26}$ represents a C5 to C22 linear, branched, or cyclic, saturated or unsaturated hydrocarbon group which may be substituted by a hydroxyl group or an amino group, or such a hydrocarbon group to which a C8 to C22 linear, branched, saturated or unsaturated fatty acid which may be substituted by a hydroxyl group is bonded at the ω-end via ester bonding; and $R^{27}$ represents a hydrogen atom or an alkyl group optionally having a substituent selected from among a hydroxyl group, a hydroxyalkoxy group, an alkoxy group, and an acetoxy group and containing 1 to 30 carbon atoms in total).

$R^{26}$ is preferably nonyl, tridecyl, pentadecyl, undecyl to which linoleic acid is bonded at the ω-position thereof via ester bonding, pentadecyl to which linoleic acid is bonded at the ω-position thereof via ester bonding, pentadecyl to which 12-hydroxystearic acid is bonded at the ω-position thereof via ester bonding, or undecyl to which branched isostearic acid is bonded at the ω-position thereof via amido bonding.

When $R^{25}$ is a hydrogen atom, $R^{27}$ is an alkyl group optionally substituted by a hydroxyl group, a hydroxyalkoxy group, an alkoxy group or an acetoxy group and containing 10 to 30 (preferably 12 to 20) carbon atoms in total. When $R^{25}$ is a C10 to C22 linear, branched, or cyclic, saturated or unsaturated hydrocarbon group which may be substituted by a hydroxyl group, $R^{27}$ is preferably a hydrogen atom or an alkyl group optionally substituted by a hydroxyl group, a hydroxyalkoxy group, an alkoxy group, or an acetoxy group and containing 1 to 8 carbon atoms in total. The hydroxyalkoxy or alkoxy group in $R^{27}$ preferably contains 1 to 7 carbon atoms.

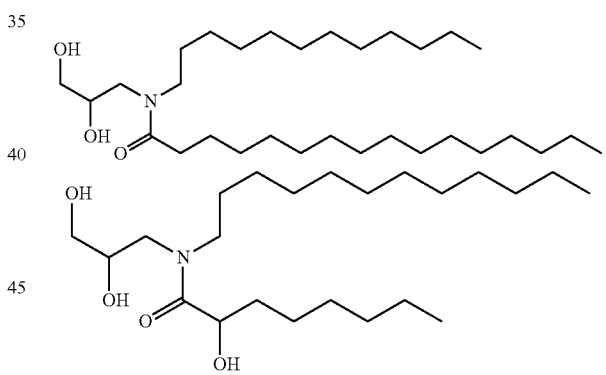

Preferred pseudo-ceramides represented by formula (5) are the case where $R^{25}$ is hexadecyl, $X^{16}$ is a hydrogen atom, $R^{26}$ is pentadecyl, and $R^{27}$ is hydroxyethyl; the case where $R^{25}$ is hexadecyl, $X^{16}$ is a hydrogen atom, $R^{26}$ is nonyl, and $R^{27}$ is hydroxyethyl; and the case where $R^{25}$ is hexadecyl, $X^{16}$ is glyceryl, $R^{26}$ is tridecyl, and $R^{27}$ is 3-methoxypropyl. More preferred pseudo-ceramides represented by formula (5) are the case where $R^{25}$ is hexadecyl, $X^{16}$ is a hydrogen atom, $R^{26}$ is pentadecyl, and $R^{27}$ is hydroxyethyl.

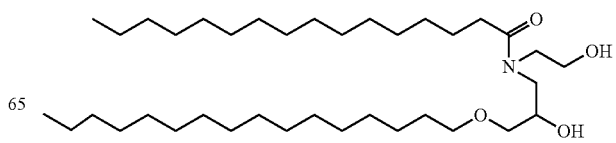

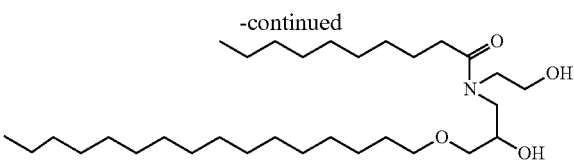

One or more species of ceramides serving as ingredient (E) may be used. The total ingredient (E) content of the composition is preferably 0.0001 to 10 mass %, more preferably 0.001 to 3 mass %, even more preferably 0.01 to 1 mass %.

The reverse vesicle composition of the present invention contains water (F) preferably in an amount of 1 to 90 mass % with respect to the total amount of the composition, more preferably 7 to 70 mass %, even more preferably 15 to 60 mass %.

The reverse vesicle composition of the present invention contains a surfactant having a molecular weight of 1,000 or less in an amount of 1 mass % or less, preferably 0.5 mass % or less, even more preferably 0.1 mass or less. When the structure formed from ingredients (A) and (B) contains a large amount of such a surfactant, the surfactant impairs the orderness of the structure. As a result, the reverse vesicle structure is not stabilized, and in some cases, the reverse vesicle structure per se fails to be formed.

In addition to the aforementioned ingredients, the reverse vesicle composition of the present invention may further contain ingredients generally employed in cosmetics. Examples of such additional ingredients include oily ingredients other than the aforementioned oily ingredients such as silicone oil; moisturizers such as 1,3-butylene glycol, propylene glycol, dipropylene glycol, glycerin, diglycerin, sorbitol, maltitol, polyethylene glycol, glycine betaine, xylytol, trehalose, mannitol, erythritol, urea, and amino acids; aqueous thickeners such as xanthane gum, hydroxyethyl cellulose, methyl cellulose, and hydroxypropyl guar gum; drug ingredients such as allantoin and tocopheryl acetate; organic material powders such as cellulose powder, nylon powder, urethane powder, cross-linked silicone powder, cross-linked methylpolysiloxane, porous cellulose powder, and porous nylon powder; powders of inorganic material such as anhydrous silica, zinc oxide, or titanium oxide; refreshing flavoring agents such as mentol and camphore; and other additives such as pH-buffers, anti-oxidants, UV-absorbers, preservatives, perfumes, sterilizing agents, and colorants.

Hitherto, production and practical use of a reverse vesicle composition have been thought to be very difficult. However, according to the present invention, a reverse vesicle composition can be produced through the following conceivable mechanism.

When ingredients (A), (B), and (C), and water are combined, a W/O emulsion is formed. When an ester oil which is in the form of liquid at 25° C. is added to the W/O emulsion, the layer formed from ingredients (A) and (B) at the water-oil interface is solubilized, to thereby be readily mixed with the oil phase, considerably reducing stability of the layer and resulting in difficulty in emulsification. Therefore, in the case where the product contains a large amount of ester oil in the form of liquid at 25° C., a sphingosine having a linear-chain alkyl group is combined with a fatty acid (particularly linear saturated fatty acid). Conceivably, in this case, interaction between alkyl chains in the layer formed from ingredients (A) and (B) is enhanced, and the bi-layer structure (bilayer membrane structure) is stabilized. In addition, a layer formed merely from ingredients (A) and (B), having high crystallinity, does not form a soft bi-layer film (bilayer membrane). However, conceivably, through incorporation of a specific amount of the ester oil, the crystallinity of the layer decreases to a certain degree, and a soft bi-layer film (bilayer membrane) can be produced, whereby a stable reverse vesicle composition can be produced.

As compared with simple application of a W/O emulsion to the skin, the reverse vesicle composition of the present invention exhibits a higher skin-permeation property. As a result, skin occlusive effect can be enhanced, whereby the barrier function of the skin and moisturized sensation of the skin can be enhanced. In W/O emulsion, water is dispersed in oil, and at the interface therebetween, a hydrophilic portion of a hydrophobic surfactant is oriented toward water (inside), while a hydrophobic portion thereof is oriented toward oil (outside). In contrast, the reverse vesicle composition has a liquid crystal structure at the W/O interface, and assumes a lipid bi-layer film whose hydrophobic portions are oriented toward both the inside and outside. Thus, the continuous phase and the enclosed phase assume an oil phase. Therefore, as compared with a conventional W/O emulsion, the reverse vesicle composition is highly compatible with the skin, and permeability of the composition is enhanced by virtue of the liquid crystal structure formed at the W/O interface.

The reverse vesicle composition of the present invention may be produced through mixing ingredients (A) to (D) and optional ingredient (E), to thereby form an oil phase; heating the oil phase at a temperature at which the ingredients are dissolved or higher; adding, to the oil phase, an aqueous phase which contains ingredient (F) and an optional water-soluble ingredient and which has been heated to a temperature equivalent to the temperature of the oil phase, to thereby form an emulsion; and cooling the emulsion to room temperature. When the emulsion is cooled to room temperature, the rotation rate of the employed stirring apparatus is controlled while the conditions of the emulsion are visually observed so as to prevent discharge of water. The rotation rate is preferably adjusted such that power consumption per unit volume of the emulsion is controlled to fall within a range of 1,000 W/m$^3$/h (W: watts required for stirring, m$^3$: volume of the composition stirred, and h: time) to 100,000 W/m$^3$/h, more preferably 3,000 W/m$^3$/h to 50,000 W/m$^3$/h. More specifically, the rotation rate of the stirring apparatus (e.g., homogenizer, propeller, etc.) may be adjusted by monitoring the indicated current amperage (A).

Formation of the reverse vesicle may be confirmed through a method generally employed for observing liquid crystal. For example, during observation of the composition through polarization microscopy, when anisotropy at the vesicle interface (i.e., an anisotropic pattern attributed to a structure indicating the presence of non-reverse micelle) is observed, formation of the reverse vesicle can be confirmed. More specifically, formation of the reverse vesicle can be confirmed by the presence of a Maltese cross (allowing more clear observation, by observation under an electron microscope, etc.).

The reverse vesicle composition of the present invention may be used as a cosmetic product, a pharmaceutical product, etc. Particularly, the composition of the present invention is preferably employed as a cosmetic product such as a milky lotion, cream, foundation, hair cream, etc., more preferably as a cream-type cosmetic product.

EXAMPLES

Examples 1 to 8, and Comparative Examples 1 to 4

Compositions each having a formulation as shown in Tables 1 and 2 were produced. Formation of a reverse vesicle and the stability of the formed vesicle formation were confirmed with respect to the produced compositions. Tables 1 and 2 also show the results.

(Production Method)

In the production of each composition, oil phase ingredients (A), (B), (C), and (D) were heated at 90° C. for melting, and the melt was stirred, to thereby form a uniform oily mixture. An aqueous phase ingredient which had been heated to 90° C. was added to the oily mixture, and the resultant mixture was emulsified. Subsequently, the emulsion was cooled at a cooling rate of 1 degree/min. During cooling, the rotation rate was adjusted so as to prevent water discharge through application of shear, whereby the power consumption per volume was adjusted to about 3,000 W/m$^3$/h. As a production apparatus, an agi-homo-mixer 2M-2 (2L size) (product of Tokushukika) was employed.

(Evaluation Methods)

(1) Formation of Reverse Vesicle:

Each as-produced composition was observed through a method generally employed for observing liquid crystal under a polarization microscope, whereby formation of reverse vesicle was confirmed.

(2) Stability:

Each composition was allowed to stand for one week at 50° C., room temperature (25° C.), and −5° C. The appearance of the composition was visually observed and evaluated on the basis of the following ratings. Specifically, the number of reverse vesicles remaining after one week storage and observed in a vision field (×100) under a polarization microscopy was counted, and percent reverse vesicle remaining was calculated with respect to 100%, corresponding to the number of reverse vesicles observed immediately after the production of the composition and in a vision field (×100) under a polarization microscopy.

A: 60% or more of reverse vesicles remained

B: 10% or more, but less than 60% of reverse vesicles remained

C: Virtually no reverse vesicle was observed

TABLE 1

|  | Ingredients (mass %) | Examples 1 | Examples 2 | Examples 3 | Comparative Examples 1 | Comparative Examples 2 |
|---|---|---|---|---|---|---|
|  | Alkyl-branch pseudo-sphingosine*[1] |  |  |  | 0.2 |  |
| A | Sphingosine |  |  | 0.2 |  |  |
| A | Phytosphingosine | 0.2 | 0.2 |  |  | 0.2 |
|  | Myristic acid |  |  |  |  | 0.3 |
| B | Palmitic acid |  | 0.3 |  | 0.3 |  |
| B | Behenic acid | 0.3 |  | 0.3 |  |  |
| C | Squalane | 6 | 6 | 6 | 6 | 6 |
| C | Liquid isoparaffin | 3 | 3 | 3 | 3 | 3 |
| D | Cholesteryl isostearate | 1 | 1 | 1 | 1 | 1 |
| E | Pseudo-ceramide*[2] | 0.4 | 0.4 | 0.4 | 0.4 | 0.4 |
|  | Dimethylpolysiloxane (6cs) | 5 | 5 | 5 | 5 | 5 |
|  | Dimethylcyclopolysiloxane (D5) | 8.4 | 8.4 | 8.4 | 8.4 | 8.4 |
|  | Silicone polymer (KSG16) | 5 | 5 | 5 | 5 | 5 |
|  | Glycerin | 16 | 16 | 16 | 16 | 16 |
|  | Dipropylene glycol | 3 | 3 | 3 | 3 | 3 |
|  | Purified water | balance | balance | balance | balance | balance |
|  | Total | 100 | 100 | 100 | 100 | 100 |
|  | (C)/(D) | 9 | 9 | 9 | 9 | 9 |
|  | Presence of reverse vesicle | yes | yes | yes | no | no |
|  | Stability: 50° C. | A | B | A | C | C |
|  | 25° C. | A | B | A | C | C |
|  | −5° C. | A | B | A | C | C |

*[1](formula)

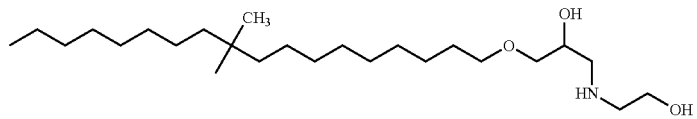 [SMILES: CCCCCCCCC(C)(C)CCCCCCCCCOCC(O)CNCCO]

*[2]Compound represented by formula (5) ($R^{25}$ = hexadecyl; $X^{16}$ = hydrogen; $R^{26}$ = pentadecyl; and $R^{27}$ = hydroxyethyl)

TABLE 2

|  | Ingredients (mass %) | Examples 4 | Examples 5 | Examples 6 | Examples 7 | Examples 8 | Comp. Exs. 3 | Comp. Exs. 4 |
|---|---|---|---|---|---|---|---|---|
| A | Phytosphingosine | 0.2 | 0.2 | 0.2 | 0.2 | 0.2 | 0.2 | 0.2 |
| B | Behenic acid | 0.3 | 0.3 | 0.3 | 0.3 | 0.3 | 0.3 | 0.3 |
| C | Squalane | 6 | 6 | 6 | 2 | 9 | 15 | 6 |
| C | Liquid isoparaffin | 3 | 3 | 3 | 1 | 4.5 | 16 | 3 |
| D | Cholesteryl isostearate | 0.13 | 0.3 | 0.9 | 3 | 0.015 | 0.03 | 10 |
| E | Pseudo-ceramide*[2] | 0.4 | 0.4 | 0.4 | 0.4 | 0.4 | 0.4 | 0.4 |
|  | Dimethylpolysiloxane (6cs) | 5 | 5 | 5 | 5 | 5 | 5 | 5 |
|  | Dimethylcyclopolysiloxane (D5) | 8.4 | 8.4 | 8.4 | 8.4 | 8.4 | 8.4 | 8.4 |

TABLE 2-continued

| | Examples | | | | | Comp. Exs. | |
|---|---|---|---|---|---|---|---|
| Ingredients (mass %) | 4 | 5 | 6 | 7 | 8 | 3 | 4 |
| Silicone polymer (KSG16) | 5 | 5 | 5 | 5 | 5 | 5 | 5 |
| Dimethicone copolyol (BY11-030) | 2 | 2 | 2 | 2 | 2 | 2 | 2 |
| Glycerin | 16 | 16 | 16 | 16 | 16 | 16 | 16 |
| Dipropylene glycol | 3 | 3 | 3 | 3 | 3 | 3 | 3 |
| Purified water | balance | balance | balance | balance | balance | balance | balance |
| Total | 100 | 100 | 100 | 100 | 100 | 100 | 100 |
| (C)/(D) | 70 | 30 | 10 | 1 | 900 | 1,033 | 0.9 |
| Presence of reverse vesicle | yes | yes | yes | yes | yes | no | no |
| Stability: 50° C. | A | A | A | B | B | C | C |
| 25° C. | A | A | A | B | B | C | C |
| −5° C. | A | A | A | B | B | C | C |

Example 9

Skincare Cream

A skincare cream having the following formulation was produced through the same method as employed for producing the compositions of Examples 1 to 8.
(C)/(D)=9

| (Ingredients) | |
|---|---|
| Phytosphingosine | 0.1 (mass %) |
| Behenic acid | 0.15 |
| Pseudo-ceramide*2 | 0.4 |
| Squalane | 6 |
| Liquid isoparaffin | 3 |
| Dimethylpolysiloxane (6cs) | 5 |
| Decamethylcyclopentanesiloxane | 8.4 |
| Silicone polymer (KSG16) | 5 |
| Cholesteryl isostearate | 1 |
| Glycerin | 16 |
| Dipropylene glycol | 3 |
| Water | balance |

Example 10

Skincare Cream

A skincare cream having the following formulation was produced through the same method as employed for producing the compositions of Examples 1 to 8.
(C)/(D)=9

| (Ingredients) | |
|---|---|
| Phytosphingosine | 0.05 (mass %) |
| Behenic acid | 0.075 |
| Pseudo-ceramide*2 | 0.4 |
| Squalane | 6 |
| Liquid isoparaffin | 3 |
| Dimethylpolysiloxane (6cs) | 5 |
| Decamethylcyclopentanesiloxane | 8.4 |
| Silicone polymer (KSG16) | 5 |
| Cholesteryl isostearate | 1 |
| Glycerin | 16 |
| Dipropylene glycol | 3 |
| Water | balance |

Example 11

UV-Protect Cream

A UV-protect cream having the following formulation was produced through the same method as employed for producing the compositions of Examples 1 to 8.
(C)/(D)=1.3

| (Ingredients) | |
|---|---|
| Phytosphingosine | 0.05 (mass %) |
| Behenic acid | 0.075 |
| Octyl methoxycinnamate | 5 |
| t-Butylmethoxybenzoylmethane | 1 |
| PEG•PPG-19/19 dimethicone | 5.2 |
| Pseudo-ceramide*2 | 7 |
| Liquid isoparaffin | 3 |
| Magnesium stearate | 1 |
| Squalane | 3 |
| Paraffin wax | 0.5 |
| Dimethicone/vinyldimethicone cross-polymer | 5 |
| Dimethylpolysiloxane (6cs) | 5 |
| Decamethylcyclopentanesiloxane | 9 |
| Glycerin | 15 |
| Dipropylene glycol | 3 |
| *Thujopsis dolabrata* extract | 2 |
| Seaweed extract | 1 |
| *Eucalyptus* extract | 1 |
| Magnesium sulfate | 1 |
| Methyl p-oxybenzoate | 0.25 |
| Tocopherol | 0.1 |
| Perfume | 0.075 |
| Water | balance |

In all the cream products of Examples 9 to 11, a reverse vesicle structure was observed. In addition, these products exhibited excellent stability in a wide temperature range, and gave good sensation in use thereof.

The invention claimed is:

1. A reverse vesicle composition comprising the following ingredients (A), (B), (C), (D), and (F):

(A) a sphingosine represented by formula (1):

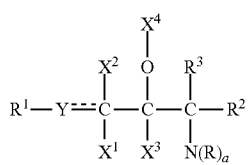

from 0.001 to 10 mass % based on the total composition,
wherein $R^1$ represents a C4 to C30 linear alkyl group which may be substituted by a hydroxyl group, a carbonyl group, or an amino group; Y represents a methylene group, a methine group, or an oxygen atom; each of $X^1$, $X^2$, and $X^3$ represents a hydrogen atom, a hydroxyl group, or an acetoxy group; $X^4$ represents a hydrogen atom, an acetyl group, or a glyceryl group, or forms an oxo group together with the adjacent oxygen atom;
wherein when Y is a methine group, one of $X^1$ and $X^2$ is a hydrogen atom, and the other is absent, and when $X^4$ forms an oxo group, $X^3$ is absent;
each of $R^2$ and $R^3$ represents a hydrogen atom, a hydroxyl group, a hydroxymethyl group, or an acetoxymethyl group; a is a number of 2 or 3; each of $(R)_a$ represents a hydrogen atom, an amidino group, or a linear-chain alkyl group optionally having a substituent selected from the group consisting of a hydroxyl group, a hydroxyalkoxy group, an alkoxy group, and an acetoxy group and containing 1 to 8 carbon atoms in total; and the broken line represents an optional unsaturated bond,
(B) a C16 to C30 fatty acid, from 0.001 to 10 mass % based on the total composition,
(C) a hydrocarbon oil, from 0.1 to 50 mass % based on the total composition,
(D) an ester oil which is in liquid form at 25° C., from 0.01 to 50 mass % based on the total composition, and
(F) water,
wherein the ratio by mass of ingredient (C) to ingredient (D) satisfies the following relationship: $1 \leq (C)/(D) < 1000$, and the composition contains a surfactant having a molecular weight of 1,000 or less in an amount of 1 mass % or less, and wherein the reverse vesicle composition has a reverse vesicle structure in which the vesicle interface is a lipid bi-layer membrane and in which there is anisotropy at the vesicle interface.

2. The reverse vesicle composition according to claim 1, which further comprises, as ingredient (E), a ceramide represented by formula (2):

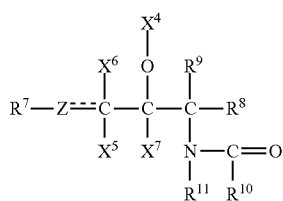

wherein $R^7$ represents a hydrogen atom or a C4 to C30 linear, branched or cyclic, saturated or unsaturated hydrocarbon group which may be substituted by a hydroxyl group, a carbonyl group, or an amino group; Z represents a methylene group, a methine group, or an oxygen atom; each of $X^5$, $X^6$, and $X^7$ represents a hydrogen atom, a hydroxyl group, or an acetoxy group; $X^4$ represents a hydrogen atom, an acetyl group, or a glyceryl group, or forms an oxo group together with the adjacent oxygen atom;
wherein when Z is a methine group, one of $X^5$ and $X^6$ is a hydrogen atom, and the other is absent, and when $X^4$ forms an oxo group, $X^7$ is absent;
each of $R^8$ and $R^9$ represents a hydrogen atom, a hydroxyl group, a hydroxymethyl group, or an acetoxymethyl group; $R^{10}$ represents a C5 to C60 linear, branched or cyclic, saturated or unsaturated hydrocarbon group which may be substituted by a hydroxyl group, a carbonyl group, or an amino group, and which may have an ether bond, an ester bond, or an amido bond in a main chain thereof; $R^{11}$ represents a hydrogen atom or a linear-chain or branched-chain, saturated or unsaturated hydrocarbon group optionally having a substituent selected from the group consisting of a hydroxyl group, a hydroxyalkoxy group, an alkoxy group, and an acetoxy group and containing 1 to 30 carbon atoms in total;
wherein, when $R^7$ is a hydrogen atom and Z is an oxygen atom, $R^{11}$ is a hydrocarbon group having 10 to 30 carbon atoms in total, and when $R^7$ is a hydrocarbon group, $R^{11}$ is a hydrocarbon group having 1 to 8 carbon atoms in total; and the broken line represents an optional unsaturated bond.

3. The reverse vesicle composition according to claim 1, wherein the ingredient (A) is contained in the amount of 0,01 to 3 mass % based on the total composition.

4. The reverse vesicle composition according to claim 1, wherein ingredient (A) is sphingosine.

5. The reverse vesicle composition according to claim 1, wherein ingredient (A) is phytosphingosine.

6. The reverse vesicle composition according to claim 1, wherein said reverse vesicle contains ingredient (B) in an amount of 0,01 to 3 mass % based on the total composition.

7. The reverse vesicle composition according to claim 1, wherein said reverse vesicle contains ingredient (C) in an amount of 0.1 to 30 mass % based on the total composition.

8. The reverse vesicle composition according to claim 1, wherein said reverse vesicle contains ingredient (D) in an amount of 0.01 to 30 mass % based on the total composition.

9. The reverse vesicle composition according to claim 1, wherein the ratio by mass of ingredient (C) to ingredient (D) is within a range in which $1 < (C)/(D) < 70$.

10. The reverse vesicle composition according to claim 9 wherein the ratio by mass of ingredient (C) to ingredient (D) is within a range in which $1 \leq (C);D) < 30$.

11. The reverse vesicle composition according to claim 1, wherein the fatty acid (B) is a C16 to C22 saturated or unsaturated fatty acid.

12. A reverse vesicle composition comprising ingredients (A), (B), (C) (D), and (F), wherein the ingredient (A) is a sphingosine represented by formula (3):

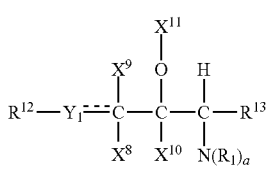

wherein $R^{12}$ represents a C7 to C24 linear alkyl group which may be substituted by a hydroxyl group; $Y_1$ represents a methylene group or a methine group; each of $X^8$ $X^9$, and $X^{10}$ represents a hydrogen atom, a hydroxyl group, or an acetoxy group; $X^{11}$ represents a hydrogen atom or forms an oxo group together with the adjacent oxygen atom wherein when $Y^1$ is a methine group, one of $X^8$ and $X^9$ is a hydrogen atom, and the other is absent, and when $X^{11}$ forms an oxo group, $X^{10}$ is absent; $R^{13}$ represents a hydroxymethyl group or an acetoxymethyl group; a is a number of 2 or 3; each of $(R_1)$a represents a hydrogen atom, an amidino group, or a linear alkyl group optionally having a substituent selected from the group consisting of a hydroxyl group, a hydroxyalkoxy group, an alkoxy group, and an acetoxy group and containing 1 to 4 carbon atoms in total; and the broken line represents an optional unsaturated bond, (B) a C16 to C30 fatty acid, from 0.001 to 10 mass % based on the total composition, (C) a hydrocarbon oil, from 0.1 to 50 mass % based on the total composition, (D) an ester oil which is in liquid form at 25° C., from 0.01 to 50 mass % based on the total composition, and (F) water, wherein the ratio by mass of ingredient (C) to ingredient (D) satisfies the following relationship: $1 \leq (C)/(D) < 1000$, and the composition containis a surfactant having a molecular weight of 1,000 or less in an amount of 1 mass % or less, and wherein the reverse vesicle composition has a reverse vesicle structure in which the vesicle interface is a lipid bi-layer membrane and in which there is anisotropy at the vesicle interface.

13. The reverse vesicle composition according to claim 12, wherein the sphingosine represented by formula (3) is selected from the group consisting of sphingosine, dihydrosphingosine, phytosphingosine, sphingadienine, dehydrosphingosine, and dehydrophytosphingosine, and N-alkyl derivatives thereof.

14. A method for producing a reverse vesicle composition, the composition comprising the following ingredients (A), (B), (C), (D), and (F):

(A) a sphingosine represented by formula (1):

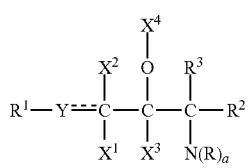

(1)

wherein $R^1$ represents a C4 to C30 linear-chain alkyl group which may be substituted by a hydroxyl group, a carbonyl group, or an amino group; Y represents a methylene group, a methine group, or an oxygen atom; each of $X^1$, $X^2$, and $X^3$ represents a hydrogen atom, a hydroxyl group, or an acetoxy group; $X^4$ represents a hydrogen atom, an acetyl group, or a glyceryl group, or forms an oxo group together with the adjacent oxygen atom;

wherein when Y is a methine group, one of $X^1$ and $X^2$ is a hydrogen atom, and the other is absent, and when $X^4$ forms an oxo group, $X^3$ is absent;

each of $R^2$ and $R^3$ represents a hydrogen atom, a hydroxyl group, a hydroxymethyl group, or an acetoxymethyl group; a is a number of 2 or 3; each of the each of $(R)_a$ represents a hydrogen atom, an amidino group, or a linear-chain alkyl group optionally having a substituent selected from among a hydroxyl group, a hydroxyalkoxy group, an alkoxy group, and an acetoxy group and containing 1 to 8 carbon atoms in total; and the broken line represents an optional unsaturated bond, (B) a C16 to C30 fatty acid, (C) a hydrocarbon oil, (D) an ester oil which is in liquid form at 25° C., and (F) water, wherein the ratio by mass of ingredient (C) to ingredient (D) satisfies the following relationship: $1 \leq (C)/(D) < 1000$, and the composition contains a surfactant having a molecular weight of 1,000 or less in an amount of 1 mass % or less, the method comprising the steps of mixing ingredients (A), (B), (C), and (D), to thereby form an oil phase; heating the oil phase at a temperature at which ingredients (A), (B), and (C) are dissolved or higher; adding, to the oil layer, an aqueous phase which contains ingredient (F) and which has been heated to a temperature equivalent to the temperature of the oil phase, to thereby form an emulsion; and cooling the emulsion to room temperature, thereby forming a reverse vesicle structure in which the vesicle interface is a lipid bi-layer membrane and in which there is anisotropy at the vesicle interface, wherein, in said reverse vesicle composition, ingredient (A) is of from 0.001 to 10 mass % based on the total composition, ingredient (B) is of from 0.001 to 10 mass % based on the total composition, ingredient(C) is of from 0.1 to 50 mass % based on the total composition, and ingredient (D) is of from 0.01 to 50 mass % based on the total composition.

15. The method for producing a composition having a reverse vesicle structure according to claim 14, Wherein, during cooling, the emulsion to room temperature, the emulsion is stirred such that the power consumption per unit volume of the emulsion falls within a range of 1,000 W/m³/h to 100,000 W/m³/h; wherein W is the watts required for stirring, m³ is the volume of the composition stirred, and h is the time.

* * * * *